(12) United States Patent
Taneda

(10) Patent No.: US 10,898,148 B2
(45) Date of Patent: Jan. 26, 2021

(54) RADIATION IMAGE CAPTURING SYSTEM

(71) Applicant: Konica Minolta, Inc., Tokyo (JP)

(72) Inventor: Atsushi Taneda, Koganei (JP)

(73) Assignee: KONICA MINOLTA, INC., Tokyo (JP)

( * ) Notice: Subject to any disclaimer, the term of this patent is extended or adjusted under 35 U.S.C. 154(b) by 227 days.

(21) Appl. No.: 15/426,453

(22) Filed: Feb. 7, 2017

(65) Prior Publication Data

US 2017/0238892 A1 Aug. 24, 2017

(30) Foreign Application Priority Data

Feb. 18, 2016 (JP) ................................. 2016-028512

(51) Int. Cl.
*A61B 6/00* (2006.01)

(52) U.S. Cl.
CPC ............ *A61B 6/463* (2013.01); *A61B 6/4283* (2013.01); *A61B 6/4405* (2013.01); *A61B 6/465* (2013.01); *A61B 6/467* (2013.01); *A61B 6/563* (2013.01)

(58) Field of Classification Search
None
See application file for complete search history.

(56) References Cited

U.S. PATENT DOCUMENTS

| | | | |
|---|---|---|---|
| 2016/0143602 A1* | 5/2016 | Hiroike | A61B 6/463 378/98.5 |
| 2016/0180021 A1* | 6/2016 | Higano | G06F 16/51 707/722 |
| 2017/0164916 A1* | 6/2017 | Kosuge | A61B 6/467 |
| 2017/0262436 A1* | 9/2017 | Uchida | G06F 16/22 |

FOREIGN PATENT DOCUMENTS

| | | |
|---|---|---|
| JP | 2004337232 A | 12/2004 |
| JP | 2011050528 A | 3/2011 |
| JP | 2012135697 A | 7/2012 |
| JP | 2015195811 A | 11/2015 |
| WO | 2014208722 A1 | 12/2014 |

OTHER PUBLICATIONS

JPO, Notification of Reasons for Refusal for the corresponding Japanese patent application No. 2016-028512, dated Nov. 12, 2019, with English translation (7 pages).
JPO, Office Action for the corresponding Japanese patent application No. 2016-028512, dated Apr. 21, 2020, with English translation (5 pages).

* cited by examiner

*Primary Examiner* — Hoon K Song
(74) *Attorney, Agent, or Firm* — Lucas & Mercanti, LLP

(57) ABSTRACT

A radiation image capturing system includes the following. An input unit is used to input that a captured radiation image is a capturing failure. A storage stores irradiating amount information regarding capturing set as the capturing failure when there is input that the captured radiation image is the capturing failure. An output unit outputs the irradiating amount information regarding the capturing set as the capturing failure stored in the storage.

14 Claims, 15 Drawing Sheets

FIG.3

| | | | | | | |
|---|---|---|---|---|---|---|
| L1 | D(1,1) | D(1,2) | D(1,3) | D(1,4) | D(1,5) | |
| L2 | D(2,1) | D(2,2) | D(2,3) | D(2,4) | D(2,5) | |
| L3 | D(3,1) | D(3,2) | D(3,3) | D(3,4) | D(3,5) | |
| L4 | D(4,1) | D(4,2) | D(4,3) | D(4,4) | D(4,5) | |
| L5 | D(5,1) | D(5,2) | D(5,3) | D(5,4) | D(5,5) | |
| L6 | D(6,1) | D(6,2) | D(6,3) | D(6,4) | D(6,5) | |
| L7 | D(7,1) | D(7,2) | D(7,3) | D(7,4) | D(7,5) | |
| L8 | D(8,1) | D(8,2) | D(8,3) | D(8,4) | D(8,5) | |
| L9 | D(9,1) | D(9,2) | D(9,3) | D(9,4) | D(9,5) | |
| L10 | D(10,1) | D(10,2) | D(10,3) | D(10,4) | D(10,5) | |
| L11 | D(11,1) | D(11,2) | D(11,3) | D(11,4) | D(11,5) | |
| L12 | D(12,1) | D(12,2) | D(12,3) | D(12,4) | D(12,5) | |

FIG.6

| CAPTURING ORDER ID | PATIENT ID | PATIENT NAME | SEX | AGE | DEPARTMENT | CAPTURING SITE | CAPTURING DIRECTION | CAPTURING DATE |
|---|---|---|---|---|---|---|---|---|
| 001 | 100085 | M | MALE | 25 | SURGERY | CHEST | FRONT P → A | OOOO/OO/OO |
| 002 | 100085 | M | MALE | 25 | SURGERY | STOMACH | FRONT P → A | OOOO/OO/OO |
| 003 | 100085 | M | MALE | 25 | SURGERY | HEAD | FRONT P → A | OOOO/OO/OO |
| 004 | 100085 | M | MALE | 25 | SURGERY | KNEE | FRONT R | OOOO/OO/OO |
| 005 | 100063 | W | FEMALE | 32 | SURGERY | CHEST | SIDE R → L | XXXX/XX/XX |
| 006 | 100063 | W | FEMALE | 32 | SURGERY | STOMACH | FRONT A → P | XXXX/XX/XX |

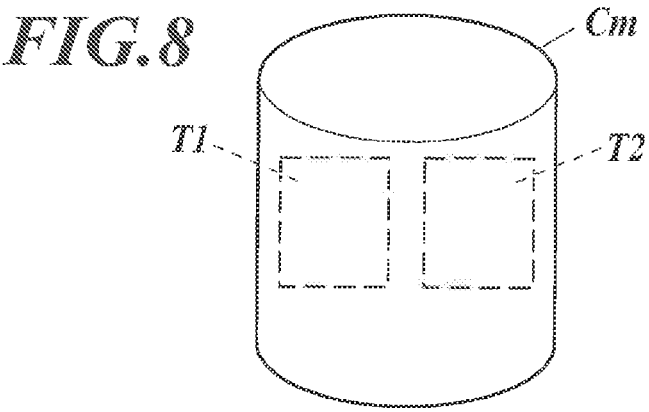

FIG.9A

| STORAGE DESTINATION | PARAMETER | CAPTURING 1 | CAPTURING 2 |
|---|---|---|---|
| LID | ID ISSUED WHEN IMAGE IS GENERATED | ... | ... |
| PERFORMED_PS_LID | CAPTURING ORDER ID | ... | ... |
| CODE_VALUE | CODE SHOWING CAPTURING SITE | ... | ... |
| CODE_MEANING | NORMAL | NORMAL | NORMAL |
| KVP | TUBE VOLTAGE | ... | ... |
| EXPOSURE_TIME | EXPOSURE TIME | ... | ... |
| XRAY_TUBE_CURRENT | TUBE CURRENT | ... | ... |
| EXPOSURE | IRRADIATING AMOUNT | ... | ... |

FIG.9B

| ATTRIBUTE NAME | TAG | VALUE |
|---|---|---|
| Performed Procedure Step Status | (0040, 0252) | EXAMINATION STATUS (COMPLETED, DISCONTINUED) |
| Study ID | (0020, 0010) | CAPTURING ORDER ID |
| Code Value | (0008, 0100) | CODE SHOWING CAPTURING SITE |
| Code Meaning | (0008, 0104) | STATUS IN CAPTURING SUCH AS NORMAL, RE-CAPTURE, ADDITIONAL CAPTURE |
| KVP | (0018, 0060) | TUBE VOLTAGE |
| Exposure Time | (0018, 1150) | EXPOSURE TIME |
| X-ray Tube Current | (0018, 1151) | TUBE CURRENT |
| Exposure | (0018, 1152) | IRRADIATING AMOUNT |
| ⋮ | ⋮ | ⋮ |

*FIG.11* T2

| STORAGE DESTINATION | PARAMETER | CAPTURING1 |
|---|---|---|
| NG_LID | ID ISSUED WHEN CAPTURING FAILURE OCCURS | ... |
| PERFORMED_PS_LID | CAPTURING ORDER ID | ... |
| NG_CODE_VALUE | CODE SHOWING CAPTURING SITE | ... |
| NG_CODE_MEANING | CAPTURING FAILURE | CAPTURING FAILURE |
| NG_KVP | TUBE VOLTAGE | ... |
| NG_EXPOSURE_TIME | EXPOSURE TIME | ... |
| NG_XRAY_TUBE_CURRENT | TUBE CURRENT | ... |
| NG_EXPOSURE | IRRADIATING AMOUNT | ... |

| STORAGE DESTINATION | PARAMETER | CAPTURING1 |
|---|---|---|
| CAPTURING FAILURE CANCEL FLAG | | 0 |
| NG_LID | ID ISSUED WHEN CAPTURING FAILURE OCCURS | ... |
| PERFORMED_PS_LID | CAPTURING ORDER ID | ... |
| NG_CODE_VALUE | CODE SHOWING CAPTURING SITE | ... |
| NG_CODE_MEANING | CAPTURING FAILURE | CAPTURING FAILURE |
| NG_KVP | TUBE VOLTAGE | ... |
| NG_EXPOSURE_TIME | EXPOSURE TIME | ... |
| NG_XRAY_TUBE_CURRENT | TUBE CURRENT | ... |
| NG_EXPOSURE | IRRADIATING AMOUNT | ... |

FIG.16B

| STORAGE DESTINATION | PARAMETER | CAPTURING1 | CAPTURING2 |
|---|---|---|---|
| CAPTURING FAILURE CANCEL FLAG | | 1 | 0 |
| NG_LID | ID ISSUED WHEN CAPTURING FAILURE OCCURS | ... | ... |
| PERFORMED_PS_LID | CAPTURING ORDER ID | ... | ... |
| NG_CODE_VALUE | CODE SHOWING CAPTURING SITE | ... | ... |
| NG_CODE_MEANING | CAPTURING FAILURE | NORMAL | CAPTURING FAILURE |
| NG_KVP | TUBE VOLTAGE | ... | ... |
| NG_EXPOSURE_TIME | EXPOSURE TIME | ... | ... |
| NG_XRAY_TUBE_CURRENT | TUBE CURRENT | ... | ... |
| NG_EXPOSURE | IRRADIATING AMOUNT | ... | ... |

RADIATION IMAGE CAPTURING SYSTEM

BACKGROUND OF THE INVENTION

Field of the Invention

The present invention relates to a radiation image capturing system.

Description of Related Art

There are radiation image capturing systems being developed in which radiation such as X-rays are irradiated from a radiation generating apparatus, the radiation passing through a subject is read as a signal value in a radiation image capturing apparatus (Flat Panel Detector) and transferred to a console, etc., and a radiation image is generated in the console, etc. based on the transferred signal value. In such radiation image capturing system, the radiation image is displayed on the display such as the console, etc., and an operator such as a radiation technician observes the displayed radiation image in order to determine whether the capturing needs to be performed again.

That is, the image may be blurred due to body movement of the patient who is the subject, there may be a mistake in the setting of the range to irradiate radiation (irradiating field) and a lesion may not be suitably captured, or amount of irradiated radiation may be too little or too much and the entire image may be too white or too black. Such radiation images cannot be used as images for diagnosis. In such case, the operator such as the radiation technician judges the image is a capturing failure and performs capturing again.

For example, Japanese Patent Application Laid-Open Publication No. 2012-135697 describes the invention in which the reason why the image is a capturing failure when such capturing failure of the image occurs is stored, and the reason stored in the storage is displayed on the display. For example, the reason of capturing failure of the image and the name of the operator who captured the image are displayed. With this, the operator acknowledges the reason why capturing failure occurred, and such reason of capturing failure occurring in capturing can be prevented.

However, the invention described in Japanese Patent Application Laid-Open Publication No. 2012-135697 merely stores the reason for capturing failure such as "irradiating amount lack", "excess irradiating amount", etc., and the statistics are prepared. The statistics of the reason for capturing failure for all of the operators, or the statistics of the reason for capturing failure for each operator is displayed to show the tendency. This merely notifies the reason of capturing failure to the user.

That is, according to the invention of Japanese Patent Application Laid-Open Publication No. 2012-135697, the actual amount of the irradiated radiation is not quantitatively managed. Therefore, for example, when the next capturing is performed on the same patient (subject) using the same capturing apparatus, it is not possible to quantitatively understand how much the irradiated radiation should be increased or decreased since the actual amount of irradiated radiation is not quantitatively managed when the capturing failure occurs.

The present invention has been made in consideration of the above problems, and one of the main objects is to provide a radiation image capturing system which can quantitatively manage an amount of irradiated radiation when capturing failure occurs.

BRIEF SUMMARY OF THE INVENTION

According to one aspect of the present invention, there is provided a radiation image capturing system including: an input unit to input that a captured radiation image is a capturing failure; a storage which stores irradiating amount information regarding capturing set as the capturing failure when there is input that the captured radiation image is the capturing failure; and an output unit which outputs the irradiating amount information regarding the capturing set as the capturing failure stored in the storage.

BRIEF DESCRIPTION OF THE DRAWINGS

The present invention will become more fully understood from the detailed description given hereinbelow and the appended drawings, and thus are not intended to define the limits of the present invention, and wherein;

FIG. 3 is a diagram describing an example of how to extract a signal value for preview;

FIG. 6 is a diagram showing an example of capturing order information;

FIG. 8 is a diagram showing a normal image irradiating amount information storage table and a capturing failure image irradiating amount information storage table are provided in a storage of the present embodiment;

FIG. 9A is a diagram showing an example of a configuration of a normal image irradiating amount information storage table;

FIG. 9B is a diagram describing a tag, a value, etc. to output RIS according to a DICOM standard;

FIG. 11 is a diagram showing an example of a configuration of a capturing failure image irradiating amount information storage table;

FIG. 14 is a diagram showing an example of a display screen provided with a capturing failure cancel button icon;

FIG. 16A is a diagram showing an example of configuration of a capturing failure image irradiating amount information storage table provided with a capturing failure cancel flag; and FIG. 16B is a diagram showing a state of a capturing failure image irradiating amount information storage table when capturing failure cancel processing is performed.

DETAILED DESCRIPTION OF PREFERRED EMBODIMENTS

An embodiment of a radiation image capturing system according to the present invention is described with reference to the drawings.

A radiation image capturing apparatus described below is a portable type including a sensor panel (not shown) in which a plurality of radiation detecting elements 7 (see later-described FIG. 2) are arranged in a two-dimensional array and stored in a case 2 (see later-described FIG. 1). The present invention is not limited to the above, and for example, a dedicated type (mounted type) radiation image capturing apparatus in which a sensor panel is formed as one with a supporting stage can be employed.

[Configuration of Radiation Image Capturing Apparatus]

First, a configuration, etc. of the radiation image capturing apparatus used in the radiation image capturing system according to the present embodiment is simply described. FIG. 1 is a perspective view showing an outer appearance of the radiation image capturing apparatus and FIG. 2 is a block diagram showing an equivalent circuit of the radiation image capturing apparatus. The radiation image capturing apparatus 1 is formed by storing a plurality of radiation detecting elements 7 (see FIG. 2) arranged two-dimensionally (matrix shape) on a sensor substrate not shown in a case 2 (see FIG. 1).

Figure 1:
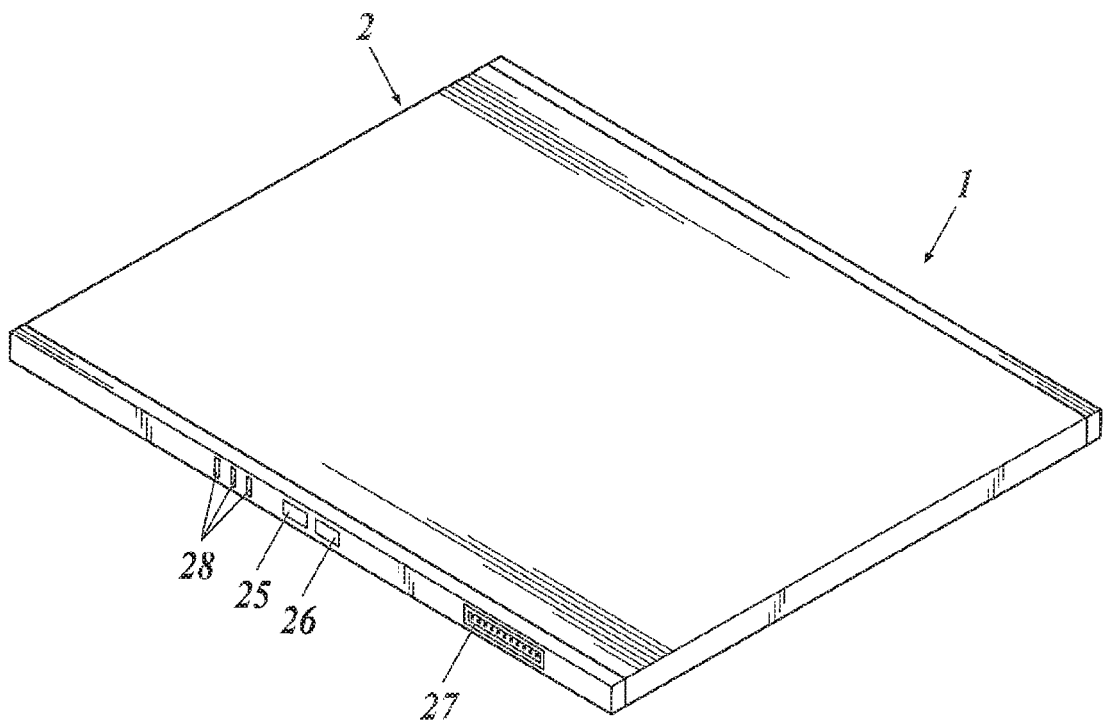
FIG. 1 is a perspective external view of a radiation image capturing apparatus used in a radiation image capturing system.
Figure 2:
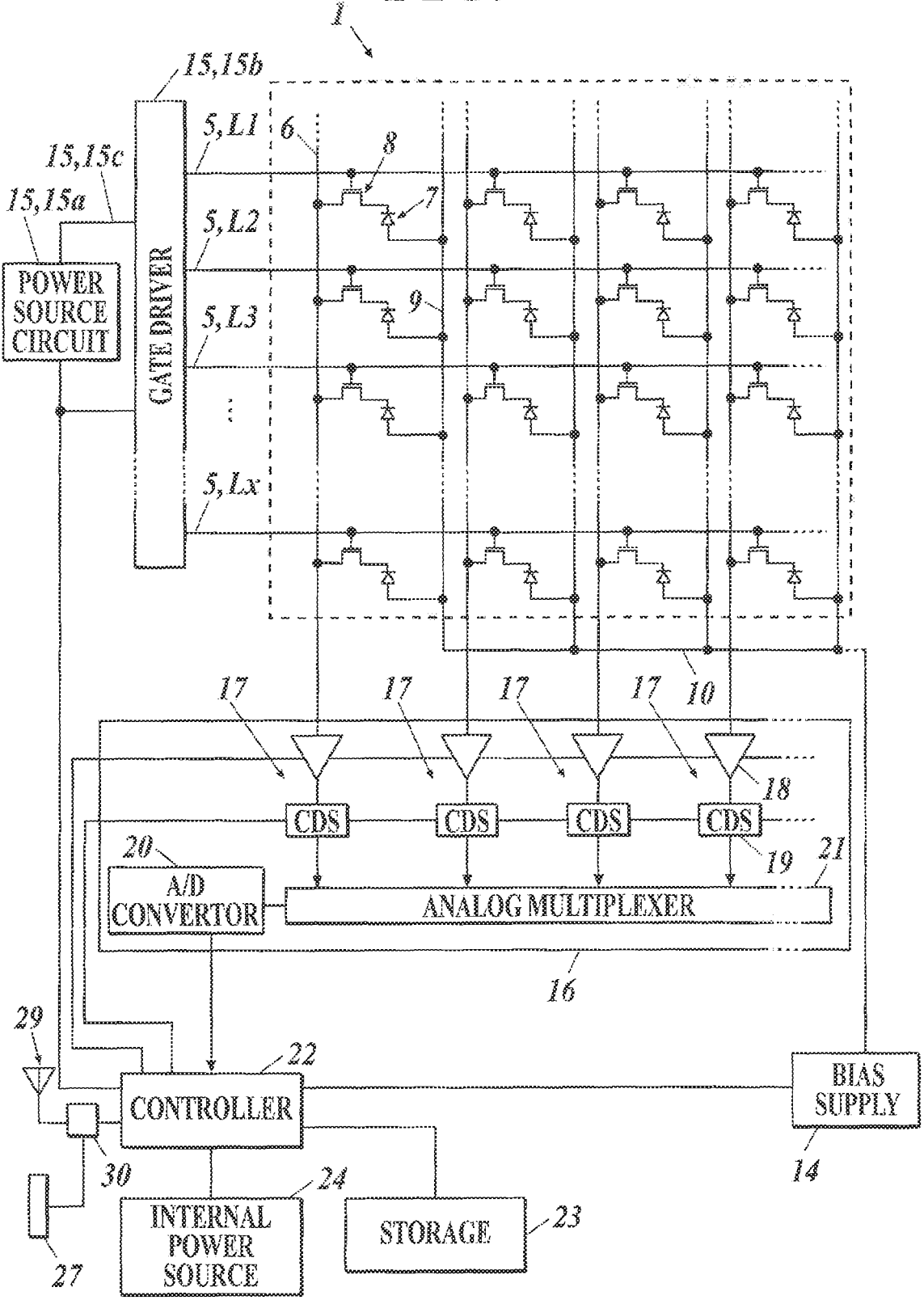
FIG. 2 is a block diagram showing an equivalent circuit of the radiation image capturing apparatus.

Then, as shown in FIG. 1, a power switch 25, a switching switch 26, a connector 27, an indicator 28, and the like are provided on one side of the case 2 of the radiation image capturing apparatus 1. Although illustration is omitted, an antenna 29 (see later-described FIG. 2) for wireless communication with external apparatuses is provided on the opposite side of the case 2.

As shown in FIG. 2, bias lines 9 are connected to each radiation detecting element 7 and reverse bias voltage is applied from the bias supply 14 through the bias line 9 and the connecting line 10. TFT (Thin Film Transistor) 8 are connected to each radiation detecting element 7 as switching elements and the TFT 8 are connected to the signal line 6. Charge according to the irradiated amount of radiation is generated in each radiation detecting element 7.

In the scanning driving unit 15, on voltage and off voltage supplied from a power source circuit 15a through lines 15c are switched in the gate driver 15b and applied to each line L1 to Lx in the scanning line 5. Then, each TFT 8 is turned off when the off voltage is applied through the scanning lines 5, conduction between the radiation detecting element 7 and the signal line 6 is cut, and the charge is accumulated in the radiation detecting element 7. When the on voltage is applied through the scanning lines 5, the state become an on state, and the charge accumulated in the radiation detecting element 7 is discharged to the signal line 6.

Each signal line 6 is connected to each readout circuit 17 in a readout IC 16. Then, when readout processing of the signal value D is performed, on voltage is sequentially applied to each line L1 to Lx of the scanning line 5 from the gate driver 15b. Then, when the TFT 8 is turned on, the charge from the radiation detecting element 7 is flown into the readout circuit 17 through the TFT 8 and the signal line 6, and the voltage value according to the amount of charge which flows in is output with the amplifying circuit 18.

Correlated double sampling circuits 19 (described with "CDS" in FIG. 2) read out and output voltage values output from the amplifying circuit 18 as analog signal values D. The output signal values D are sequentially transmitted to the A/D convertor 20 through an analog multiplexer 21. The signal values D are sequentially converted to digital values in the A/D converter 20 and sequentially stored in the storage 23.

The controller 22 includes a computer including a CPU (Central Processing Unit), a ROM (Read Only Memory), a RAM (Random Access Memory), an input/output interface and the like connected by a bus, and a FPGA (Field Programmable Gate Array) and the like (all not shown). A dedicated control circuit may be provided.

A storage 23 including a SRAM (Static RAM), SDRAM (Synchronous DRAM), a NAND type flash memory, and an internal power source 24 including a lithium ion capacitor, etc. are connected to the controller 22. A communicating unit 30 to perform wireless or wired communication with external apparatuses through the above-described antenna 29 or connector 27 is also connected to the controller 22.

The controller 22 controls applying the reverse bias voltage on each radiation detecting element 7 from the bias supply 14, and controls operation of the scanning driving unit 15, the readout circuit 17, etc. According to such control by the controller 22, the readout processing of the signal value D from each radiation detecting element 7 is performed, the readout signal value D is stored in the storage 23, or the stored signal value D is transferred to an external device through the communicating unit 30.

According to the present embodiment, when the controller 22 of the radiation image capturing apparatus 1 reads out each signal value D from each radiation detecting element 7, a preview signal value Dpre is extracted at a predetermined percentage from the read signal value D, the extracted preview signal value Dpre is transferred to the console C prior to the other signal values D, and then, the remaining signal values D are transferred to the console C. Alternatively, all of the signal values D can be transferred to the console C from the beginning without extracting the preview signal value Dpre.

For example, as a method of extracting the preview signal value Dpre as shown in FIG. 3, as shown with diagonal lines in the figure, a signal value D (n, m) read out from each radiation detecting element 7 connected to the scanning line 5 specified in a percentage of one for every predetermined number of scanning lines 5 (4 in FIG. 3) is extracted from the read out signal values D (n, m), and this can be the preview signal value Dpre.

In FIG. 3, L1, L2, . . . show lines L1, L2, . . . (see FIG. 2) of the scanning lines 5, and D (n, m) shows the signal value D read out from the radiation detecting element 7 (n, m) which is the n-th line and m-th row among the radiation detecting elements 7 in a two-dimensional array. The method of extracting the preview signal values Dpre is not limited to the above. For example, the preview signal values Dpre can be extracted at a ratio of 1 out of signal values D readout for each array of the radiation detecting elements 7 in an array of 3×3, 4×4, etc.

[Capturing Using a Radiation Image Capturing Apparatus]

Here, capturing using the above-described radiation image capturing apparatus 1 is described. The capturing can be performed in a capturing room Ra as shown in FIG. 4, and the capturing can also be performed by transporting a diagnosis car 70 on which a later-described radiation generating apparatus 52, etc. is mounted to a hospital room R1 as shown in FIG. 5.

Figure 4:
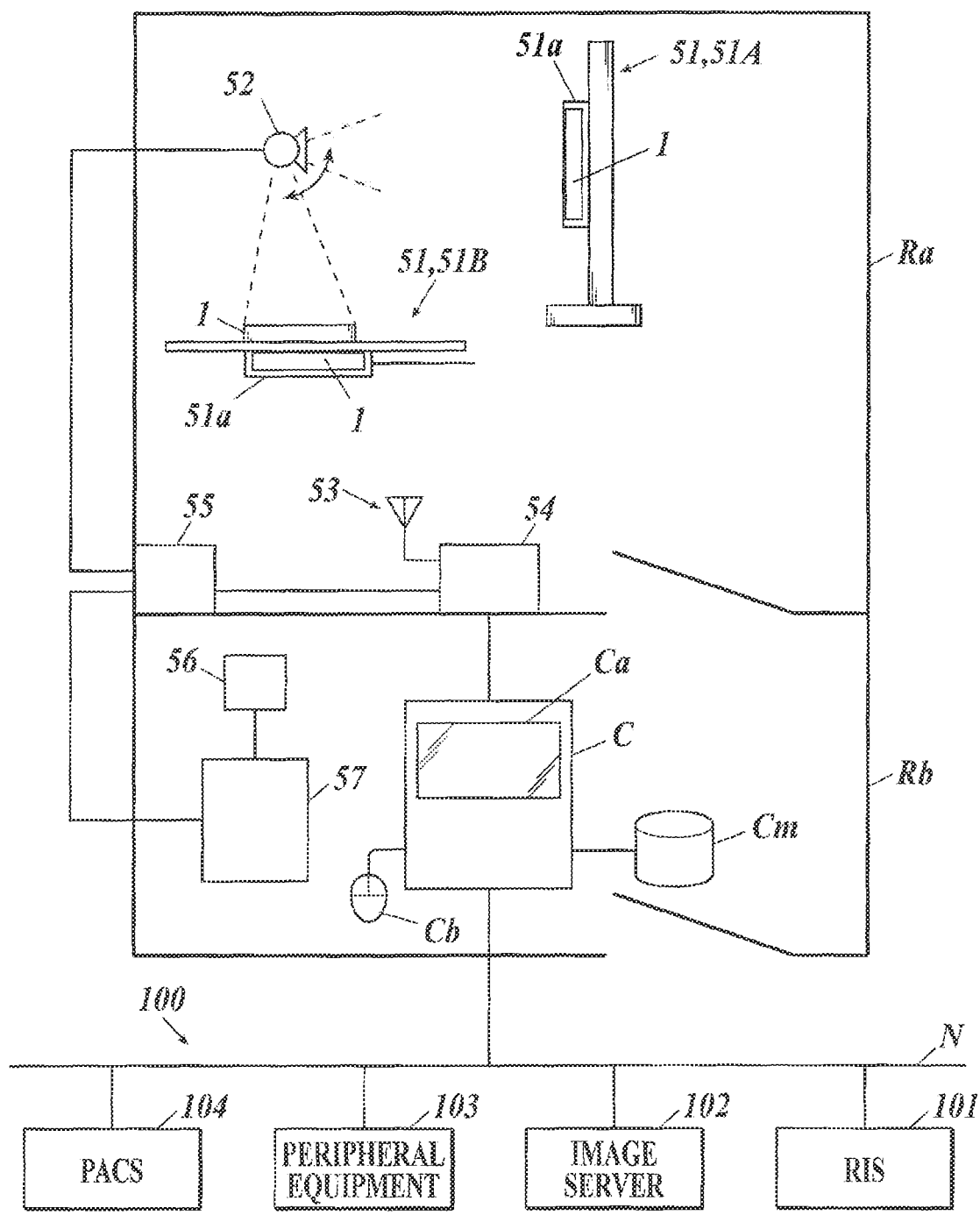
FIG. 4 is a diagram showing one configuration example of a radiation image capturing system of the present embodiment.
Figure 5:
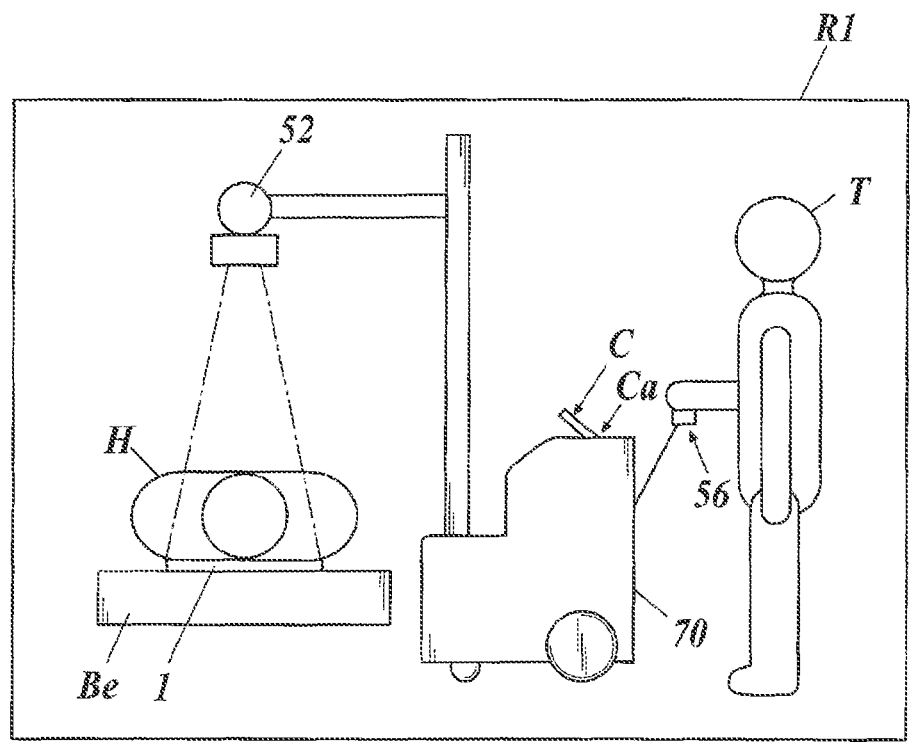
FIG. 5 is a diagram showing a diagnosis car with a radiation generating apparatus, etc. mounted thereon transported to a hospital room to perform capturing.

For example, when capturing is performed in the capturing room Ra, as shown in FIG. 4, the capturing is performed by mounting the radiation image capturing apparatus 1 in a cassette holder 51a of a capturing stand 51. According to FIG. 4, a capturing stand 51A shows a capturing stand for capturing in a standing position, and a capturing stand 51B shows a capturing stand for capturing in a lying position. For example, the radiation image capturing apparatus 1 may be inserted between the subject who lay on a plate of the capturing stand 51B for capturing in the lying position and a plate (not illustrated) and capturing may be performed.

At least one radiation generating apparatus 52 which irradiates radiation to the radiation image capturing apparatus 1 through the subject (not shown) is provided n the capturing room Ra. An access point 54 including an antenna 53 for relaying wireless or wired communication between the apparatuses in the capturing room Ra and the apparatuses outside the capturing room Ra is provided in the capturing room Ra. The communication between the radiation image capturing apparatus 1 and the access point 54 may be performed wired or wirelessly.

A generator 55 of the radiation generating apparatus 52, a console C, etc. are connected to the access point 54, and the access point 54 relays communication among the radiation image capturing apparatus 1, the console C, the generator 55, etc. of the radiation generating apparatus 52, etc.

Then, when tube voltage, tube current, exposure time, irradiating amount, etc. are set by the operator such as the radiation technician, the generator 55 of the radiation generating apparatus 52 performs various control on the radiation generating apparatus 52 such as irradiating from the radiation generating apparatus 52 the radiation with the amount of radiation according to the set tube voltage, etc.

An operation table 57 of the radiation generating apparatus 52 is provided in a front room Rb (also called an operation room, etc.). An emitting switch 56 is provided on the operation table 57 to be operated by the operator such as the radiation technician in order to instruct start of irradiation of radiation to the generator. A console C including a computer, etc. is provided in the front room Rb. The console C may be provided in the capturing room Ra or outside the front room Rb or in a room different from the capturing room Ra and the front room Rb.

A display Ca including a CRT (Cathode Ray Tube), a LCD (Liquid Crystal Display), etc. is provided in the console C and an input unit Cb such as a mouse, a keyboard, a touch panel, etc. can be connected. A storage Cm including a HDD (Hard Disk Drive) is connected to or mounted inside the console C.

Then, after adjusting the position between the patient as the subject (not shown) and the radiation image capturing apparatus 1, the operator such as the radiation technician, etc. operates the emitting switch 56, and the radiation is emitted from the radiation generating apparatus 52 and capturing is performed. Then, after capturing, the preview signal value Dpre and the remaining signal values D, etc. are transferred to the console C from the radiation image capturing apparatus 1.

As shown in FIG. 5, capturing can be performed by bringing a diagnosis car 70 on which a radiation generating apparatus 52, a console C, etc. are mounted in a hospital room R1. In this case, the generator 55, the access points 54, etc. (both not shown) are stored inside a main body unit of the diagnosis car 70.

In this case, as shown in FIG. 5, the radiation image capturing apparatus 1 is inserted between a bed Be and the patient as a subject H, or is placed against the body of the patient to be used in capturing. Then, in this case also, the operator T such as the radiation technician, etc. operates the emitting switch 56 to emit radiation from the radiation generating apparatus 52 to perform capturing, and after capturing, the preview signal value Dpre and the remaining signal values D, etc. are transmitted from the radiation image capturing apparatus 1 to the console C.

The capturing of the patient who is the subject may be performed in places in a hospital other than the capturing room Ra and the hospital room R1 such as an operating room or an emergency room.

[Regarding Radiation Image Capturing System]

Next, the radiation image capturing system 100 according to the present embodiment is described. The operation of the radiation image capturing system 100 of the present embodiment is also described. Below, an example of FIG. 4 in which the capturing is performed in the capturing room Ra is described. For example, when the diagnosis car 70 is brought into the hospital room Ra and capturing is performed as described in FIG. 5, after the capturing, the console C is connected to the communication network N shown in FIG. 4 so as to be able to establish the radiation image capturing system 100 similar to that shown in FIG. 4.

The radiation image capturing system 100 according to the present embodiment includes the above-described console C, a RIS (Radiology Information System) 101, an image server 102 which stores a radiation image p generated by the console C to be provided for diagnosis, and peripheral equipment 103 such as a viewer or a printer, the above components connected to each other to be able to communicate data through a communication network N.

A PACS (Picture Archiving and Communication System) 104, another console C (not shown), or other modality can be connected to the communication network N. Although illustration is omitted, a HIS (Hospital Information System) can be connected to the communication network N, or the HIS can be connected through a network different from the RIS.

According to the present embodiment, at least the communication between the console C, RIS 101, image server 102 and peripheral equipment 103 is performed by DICOM (Digital Imaging and Communications in Medicine) standard which is the typical standard for exchanging medical information. The present embodiment is described using the above, but the present invention is not limited to employing the DICOM standard.

Before capturing, based on the operation by the operator such as the radiation technician, the console c receives and obtains, for example, capturing order information regarding a series of capturing performed for a patient that day from the RIS 101 which is the management system. The RIS 101 manages capturing order information as shown in FIG. 6.

For example, as shown in FIG. 6, the capturing order information includes the following specified information, patient information such as "patient ID" P2, "patient name" P3, "sex" P4, "age" and birthdate P5, "department" P6, etc., and capturing conditions such as "capturing site" P7, "capturing direction" P8, "capturing date" P9, etc. Further, "capturing order ID" P1 is automatically assigned to each capturing order information in the order of reception, for example.

When the operator such as the radiation technician, etc. specifies for example, the "capturing date" P9, "patient name" P3 (or "patient ID" P2) on the console C and the specification is transmitted to the RIS 101, according to the MWM ((Modality Working Management) or MWL (Modality Work List)) function of DICOM, the RIS 101 searches the information stored in the RIS 101, selects the capturing order information specifying the above capturing date, capturing patient, etc., and transmits the capturing order information to the console C. For example, with this, the console C obtains the capturing order information regarding the series of capturing before the capturing is performed.

According to the present embodiment, actually, the console C interprets the information regarding the capturing order information transmitted in a specific form from the RIS 101 and forms the capturing order information in a state as shown in FIG. 6. When the capturing order information is transmitted from the RIS 101 to the console C, according to the DICOM standard, an examination ID (Study ID) is assigned as a number and transmitted for each capturing (that is for each capturing order information). According to the present embodiment, for ease of description, the above "capturing order ID" P1 is assigned as the examination ID. Alternatively, a number different from the capturing order ID can be assigned as the examination ID.

According to the description below, as the capturing order information regarding the series of capturing, capturing is performed based on four capturing order information regarding the patient "M" from among the capturing order information shown in FIG. 6. The "series of capturing" does not necessarily mean plurality of capturing, and may be only one capturing (in this case, "capturing order information regarding the series of capturing" is one).

When the capturing is started, based on the MPPS (Modality Performed Procedure Step) function of the DICOM, the operator such as the radiation technician, etc. specifies the capturing order information (the above 4 capturing order information in this example) for the capturing to be performed on the console C. The above is transmitted to the RIS 101 to instruct the console C to notify the start of capturing. Then, the console C attaches information such as capturing start time to the information and notifies the start of capturing to the RIS 101 (MPPS (Inprogress)). The RIS 101 answers with a signal of acknowledgment to the console C.

Then, for example, the console C controls the radiation image capturing apparatus 1 to turn on the power of the radiation image capturing apparatus 1 or starts the radiation image capturing apparatus 1 from the sleep mode to set the radiation image capturing apparatus 1 to a state in which capturing can be performed. As described above, the console C controls the radiation image capturing apparatus 1 so that capturing based on the capturing order information obtained according to the above is suitably performed.

The operator such as the radiation technician, etc. sets the tube voltage or tube current, exposure time, irradiating amount, etc. on the generator 55 of the radiation generating apparatus 52, leads the patient to the capturing room Ra, and adjusts the position between the patient and the cassette holder 51a in order to prepare for capturing. Then, the operator moves to the front room Rb and operates the emitting switch 56 to emit radiation from the radiation generating apparatus 52.

When the radiation is emitted, the generator 55 of the radiation generating apparatus 52 transmits to the console C information such as tube voltage, tube current, exposure time, irradiating amount, etc. set when the radiation is irradiated and the console C stores the information in a storage Cm (see FIG. 4), etc.

When the radiation is irradiated from the radiation generating apparatus 52 and capturing is performed, as described above, the controller 22 of the radiation image capturing apparatus 1 performs readout processing of the signal value D from the radiation detecting elements 7, extracts a preview signal value Dpre from the readout signal value D, and transfers the extracted preview signal value Dpre to the console C. The console C stores the transferred preview signal value Dpre in the storage Cm, etc. Next, when the remaining signal values D are transferred from the radiation image capturing apparatus 1 as described above, the console C stores the remaining signal values D in the storage Cm, etc.

Then, when the console C receives the preview signal value Dpre transferred from the radiation image capturing apparatus 1, simple image processing is performed on the preview signal value Dpre to generate preview radiation image ppre. Then, the preview radiation image ppre is displayed on the display Ca.

Figure 7:
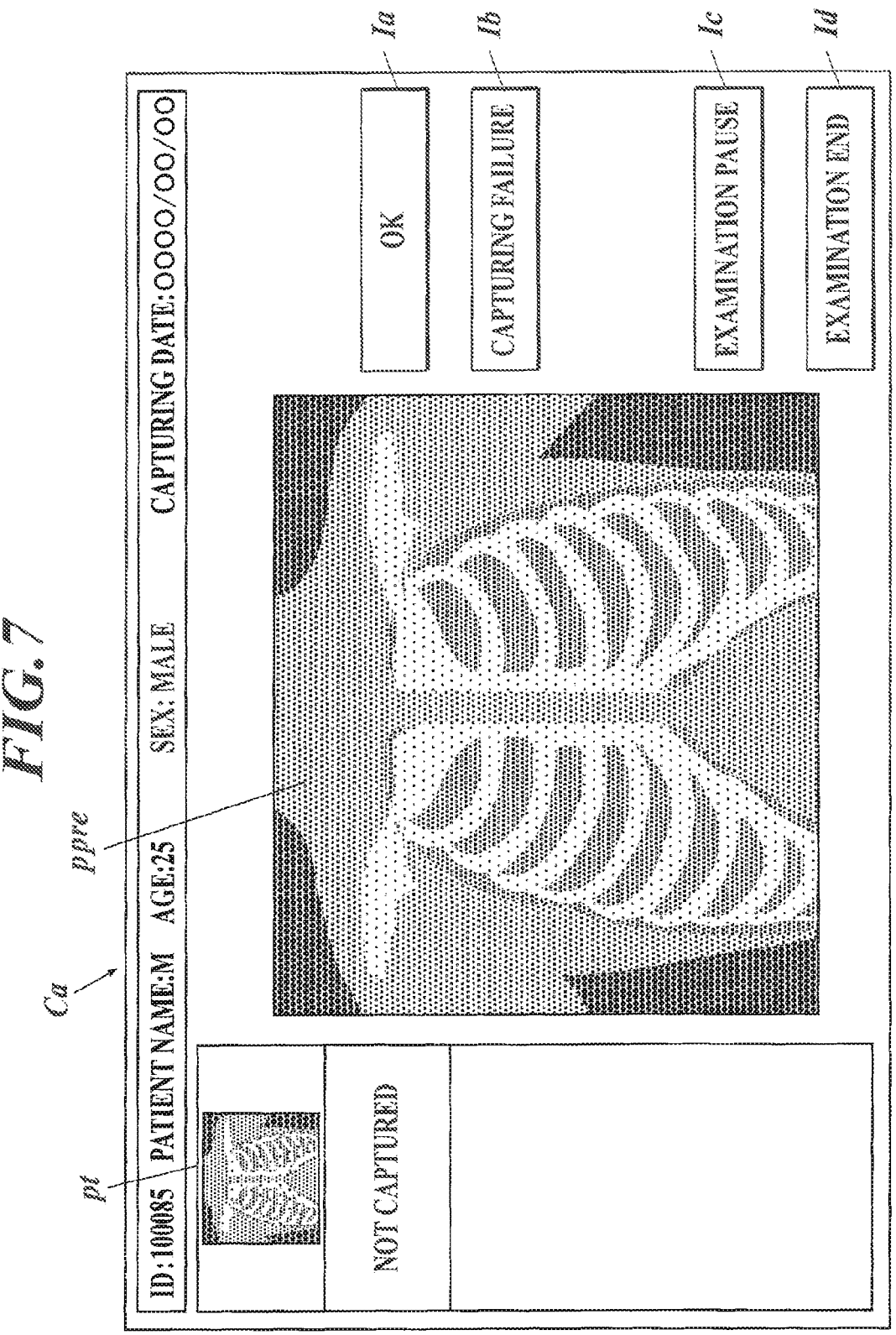
FIG. 7 is a diagram showing a configuration example of a display screen displayed on a display of a console.

Here, according to the present embodiment, the preview radiation image ppre (or the generated diagnosis radiation image p (not shown)) is displayed in the center of the display screen displayed on the display Ca of the console C as shown in FIG. 7. In the example of the display screen shown in FIG. 7, the captured preview radiation image ppre and the thumbnail image pt of the diagnosis radiation image p are displayed on the left side of the display screen.

The following is displayed on the right side of the display screen, "OK" button icon Ia clicked by the operator such as the radiation technician when the preview radiation image ppre is approved, "capturing failure" button icon Ib clicked when the preview radiation image ppre is considered to be a capturing failure, "examination pause" button icon Ic clicked when the series of capturing is paused, "examination end" button icon Id clicked when the series of capturing ends, and the like.

For example, the preview radiation image ppre and the generated diagnosis radiation image p corresponding to the thumbnail image pt may be displayed at the center of the display screen when the thumbnail image pt on the left side of the display screen is clicked. The display screen is suitably configured so that button icons to perform other processing are displayed on the display screen.

Alternatively, the console C may be configured so that the preview radiation image ppre can be considered to be approved and further processing can be performed as long as the "capturing failure" button icon Ib is not clicked by the operator such as the radiation technician. According to such configuration, the "OK" button icon Ia does not have to be provided.

[Processing when Preview Radiation Image is Approved]

Before describing processing when it is determined that the preview radiation image ppre is a capturing failure, the processing when the preview radiation image ppre is approved is described.

When the operator such as the radiation technician, etc. approves the preview radiation image ppre and the "OK" button icon Ia is clicked, or without waiting for the approval of the operator, the console C combines the preview signal value Dpre with the remaining signal values D transferred from the radiation image capturing apparatus 1 and performs image processing such as gain correction, offset correction, and gradation processing according to the capturing site on all restored original signal values D. Then, the console C generates the diagnosis radiation image p.

Although illustration is omitted, when the diagnosis radiation image p is generated, instead of the preview radiation image ppre displayed in the center of the display screen of the display Ca, the console C displays the generated diagnosis radiation image p. It is also possible to switch from the thumbnail image pt of the preview radiation image ppre to the thumbnail image pt of the diagnosis radiation image p if necessary.

After the operator such as the radiation technician adjusts the image quality of the diagnosis radiation image p according to necessity, the console C corresponds the diagnosis radiation image p with the capturing order information for the diagnosis radiation image p and stores the above in the storage Cm. The diagnosis radiation image p corresponded with the capturing order information is transmitted to the image server 102 (see FIG. 4) through the communication network N and stored in the image server 102 with the other capturing order information and the diagnosis radiation image p corresponded with the other capturing order information in the series of capturing when the capturing (examination) ends (or when the capturing (examination) is paused).

The console C stores in the storage Cm the diagnosis radiation image p corresponded with the capturing order information. The console C also stores in the storage Cm the information such as tube voltage, tube current, exposure time, irradiating amount, etc. set in the generator 55 of the radiation generating apparatus 52 when the approved preview radiation image ppre (or the diagnosis radiation image p) is captured corresponded with the capturing order ID (see FIG. 6) of the capturing order information as irradiating amount information.

Then, the irradiating amount information corresponded with the capturing order ID, etc. of the capturing order information is output to the RIS 101 (see FIG. 4) through the communication network N with the irradiating amount information corresponded with capturing order ID, etc. of the capturing order information for other capturing among the series of capturing when the capturing (examination) ends or when the capturing (examination) is paused.

As described above, according to the present embodiment, the DICOM standard is used in at least the communication between the console C and the RIS 101. Therefore, when the irradiating amount information such as the tube voltage, tube current, exposure time, irradiating amount, etc. is stored in the storage Cm corresponded with the capturing order ID, etc. of the capturing order information, the information is stored in the format suitable for the DICOM standard.

Specifically, according to the present embodiment, as shown in FIG. 8, a normal image irradiating amount information storage table T1 is provided in the storage Cm. Including the description of the "normal image irradiating amount information storage table T1", "normal" in the present application means not a capturing failure (that is, the operator such as the radiation technician, etc. approved the preview radiation image ppre). A capturing failure image irradiating amount information storage table T2 shown in FIG. 8 is described later.

Then, as shown in FIG. 9A, the console C writes and stores the parameter in each storage destination of the normal image irradiating amount information storage table T1 of the storage Cm for each capturing so that the irradiating amount information, etc. can be output to the RIS 101 by the DICOM standard.

As the irradiating amount information (that is, the irradiating amount information output to the RIS 101 later) written in the normal image irradiating amount information storage table T1, other than the information of the tube voltage, etc. set in the generator 55 of the radiation generating apparatus 52, for example, the console C and the controller 22 of the radiation image capturing apparatus 1 may derive the irradiating amount of the radiation irradiated to the radiation image capturing apparatus 1 from the signal values D read from the radiation detecting elements 7 of the radiation image capturing apparatus 1 and the irradiating amount of the derived radiation may be written in the normal image irradiating amount information storage table T1 as the irradiating amount information.

For example, a dosimeter (not shown) may be positioned near a ray source of a radiation generating apparatus 52 or a dosimeter may be positioned to a subject which is irradiated by radiation to measure the irradiating amount of radiation irradiated from the radiation generating apparatus 52 on the subject and the measured radiation irradiating amount may be written in the normal image irradiating amount information storage table T1 as the irradiating amount information.

Then, after the series of capturing ends and the adjustment of the image quality is performed on the diagnosis radiation image p, when the "examination end" button icon Id (see FIG. 7) on the display screen is clicked by the operator such as the radiation technician, etc., the console C reads the diagnosis radiation image p corresponded to the capturing order information for each capturing stored in the storage Cm. Then, as described above, the diagnosis radiation image p corresponded with the capturing order information in the series of capturing is transmitted to the image server 102 through the communication network N and stored.

In addition to the above, the console C reads out from the storage Cm the irradiating amount information, etc. (see FIG. 9A) written in the normal image irradiating amount information storage table T1 for each capturing. As shown in FIG. 9B, in order to output the above to the RIS 101 according to the DICOM standard, the console C ties each value (Value), that is, the parameter in the normal image irradiating amount information storage table T1 to tags (Tag) corresponding to attribute names (Attribute Name) and outputs the above to the RIS 101 with the information of the capturing end time, etc. (MPPS (Completed)).

Then, in this case, since the examination status output with the irradiating amount information is capturing (examination) end (Completed), the RIS 101 returns an acknowledgement signal to the console C and acknowledges that the series of capturing is finished.

The irradiating amount information output to the RIS 101 does not need to be tube voltage, tube current, exposure time, and irradiating amount as shown in FIG. 9B, and for example, may be only irradiating amount, or tube voltage other than the irradiating amount. Instead of the above, or together with the above, the irradiating amount of radiation irradiated to the radiation image capturing apparatus 1 and the irradiating amount of radiation irradiated from the radiation generating apparatus 52 to the subject can be output as the irradiating amount information.

When the "examination pause" button icon Ic (see FIG. 7) on the display screen is clicked by the operator such as the radiation technician, etc. during the series of capturing, similar to when the capturing (examination) ends, the console C reads out from the storage Cm the irradiating amount information written in the normal image irradiating amount information storage table T1 of the storage Cm for each capturing when the "examination pause" button icon Ic is clicked. As shown in FIG. 9B, the console C ties the value (that is, the parameter) to the tags corresponding to the attribute names and outputs the above with the information such as capturing pause time, etc. to the RIS 101 (MPPS (Discontinued)).

The RIS 101 returns the acknowledgment signal to the console C, but in this case, since the examination status is capturing (examination) pause (Discontinued) instead of capturing (examination) end (Completed), the RIS 101 does not acknowledge that the series of capturing is finished.

As described above, according to the present embodiment, the console C outputs the irradiating amount information for each capturing to the RIS 101 when the capturing (examination) ends or when the capturing (examination) is paused.

When the capturing (examination) is paused, the console C may transmit to the image server 102 the diagnosis radiation image p (corresponded with the capturing order information) for each capturing captured up to this point. Alternatively, the console C may collectively transmit the diagnosis radiation image p when the capturing (examination) ends.

[Processing when Determined to be Capturing Failure]

The operator such as the radiation technician, etc. determines that the captured preview radiation image ppre (or the diagnosis radiation image p captured based on the same capturing order information) is a capturing failure in the following situations, when the preview radiation image ppre (see FIG. 7) displayed on the display Ca of the console C is blurred due to body movement of the patient who is the subject, when the lesion, etc. is not suitably captured due to a mistake in the setting of the irradiating field of the radiation, or when the entire image is too white or too black due to too little or too much amount of irradiated radiation.

Figure 10:
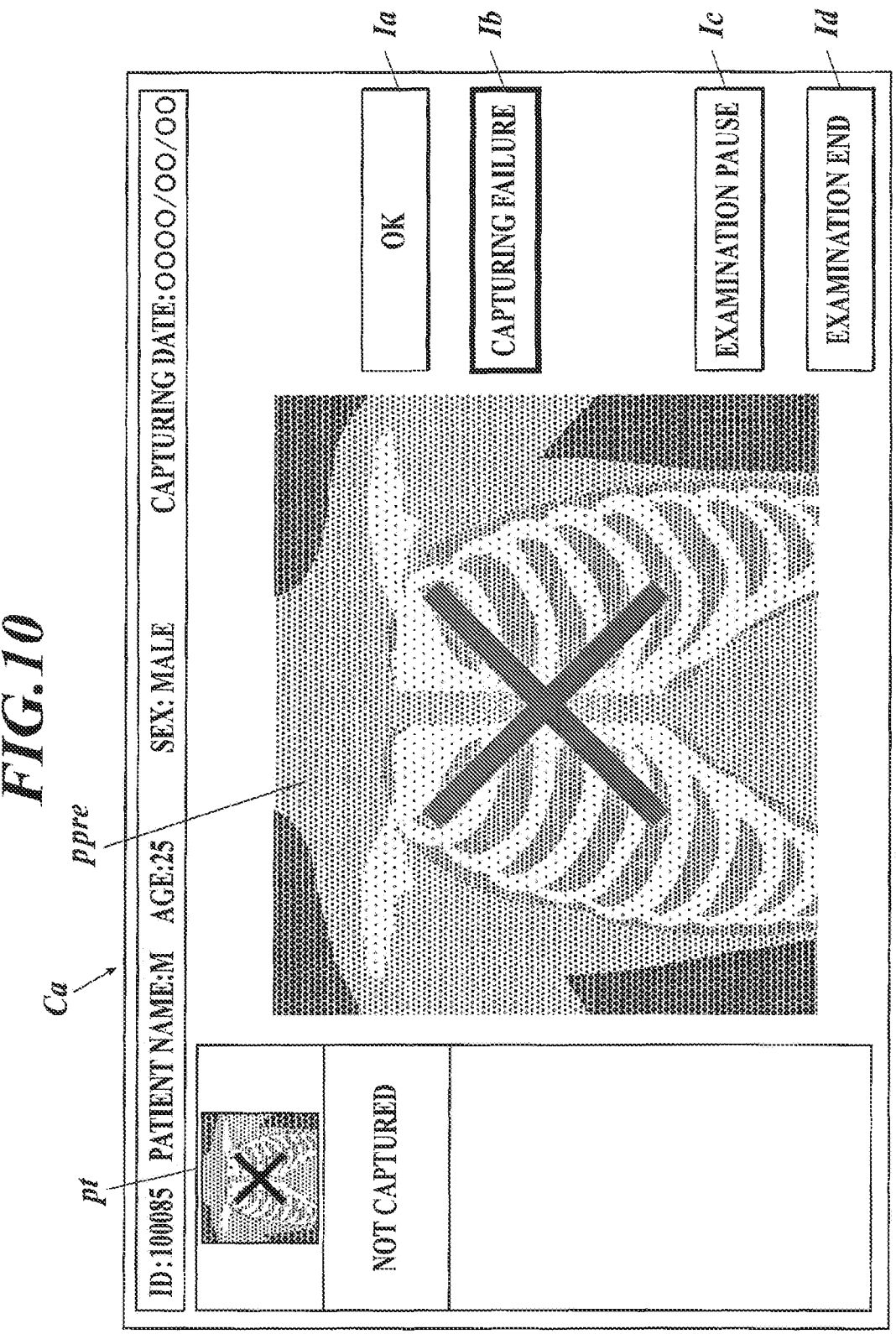
FIG. 10 is a diagram showing that an X mark is attached to a preview radiation image or thumbnail image to be displayed on the display screen when capturing failure processing is performed.

Then, in this case, the operator such as the radiation technician, etc. clicks the "capturing failure" button icon Ib on the display screen displayed on the display Ca of the console C to perform capturing failure processing and performs capturing again. According to the present embodiment, when the "capturing failure" button icon Ib is clicked, the console C may display the preview radiation image ppre, the thumbnail image pt, etc. with a x mark to clearly show that the preview radiation image ppre, etc. displayed on the display screen is a capturing failure as shown in FIG. 10, for example.

Conventionally, when the operator such as the radiation image technician, etc. performs capturing failure processing with the preview radiation image ppre, etc. considered to be the capturing failure as described above, the console C destroyed data regarding capturing related to the preview radiation image ppre considered to be the capturing failure, that is, data such as the preview signal value Dpre and the remaining signal value D (or all signal values D) transferred from the radiation image capturing apparatus 1, and irradiating amount information such as the tube voltage transmitted from the generator 55 of the radiation generating apparatus 52 after irradiating the radiation. Alternatively, either one of the signal value D or the irradiating amount information, etc. or all of the above information were stored in the storage Cm of the console C.

However, conventionally, at least the irradiating amount information when considered to be the capturing failure was not output to the RIS 101 from the console C. As described above, Japanese Patent Application Laid-Open Publication No. 2012-135697 describes when the capturing failure of the image occurs, the reason is stored and output to the RIS 101. However, only the capturing failure reason is output and the irradiating amount information when capturing failure occurs is not output to the RIS 101.

Turning to the present embodiment, when the operator such as the radiation technician determines the preview radiation image ppre or the diagnosis radiation image p is the capturing failure, the console C stores in the storage Cm the irradiating amount information regarding the capturing of the preview radiation image ppre, etc. which is the capturing failure. The console C also outputs to the RIS 101 as the management system the irradiating amount information regarding the capturing which is normal capturing and the irradiating amount information regarding the capturing of the preview radiation image ppre, etc. which is the capturing failure at the point when the series of capturing ends (capturing (examination) end) or at the point when the series of capturing is paused (capturing (examination) paused). The configuration for the above is described in detail below.

That is, according to the present embodiment, for example, as shown in FIG. 8, in addition to the above-described normal image irradiating amount information storage table T1, a capturing failure image irradiating amount information storage table T2 (see FIG. 11) is provided in the storage Cm. According to the description below, the normal image irradiating amount information storage table T1 and the capturing failure image irradiating amount information storage table T2 are provided separately in the storage Cm. Alternatively, as described later, since it is possible to discriminate whether the image is a normal image or a capturing failure image by setting the "code Meaning" to normal or capturing failure, it is possible to provide only 1 table and the normal image and the capturing failure image can be stored in one table.

When the operator such as the radiation technician, etc. determines the preview radiation image ppre (see FIG. 7) displayed on the display Ca is a capturing failure and clicks the "capturing failure" button icon Ib on the display screen, the console C writes and stores in the capturing failure image irradiating amount information storage table T2 of the storage Cm the irradiating amount information such as the tube voltage, etc. and the capturing order ID, etc. of the capturing order information transmitted from the generator 55 of the radiation generating apparatus 52 after the radiation is irradiated.

In this case, as described above, after the series of capturing, the preview radiation image ppre or the diagnosis radiation image p considered to be the capturing failure can be corresponded with the capturing order information and transmitted to and stored in the image server 102 (see FIG. 4) together with the normally captured radiation image p corresponded with the capturing order information. Alternatively, the image considered to be the capturing failure can be destroyed.

Figure 12:
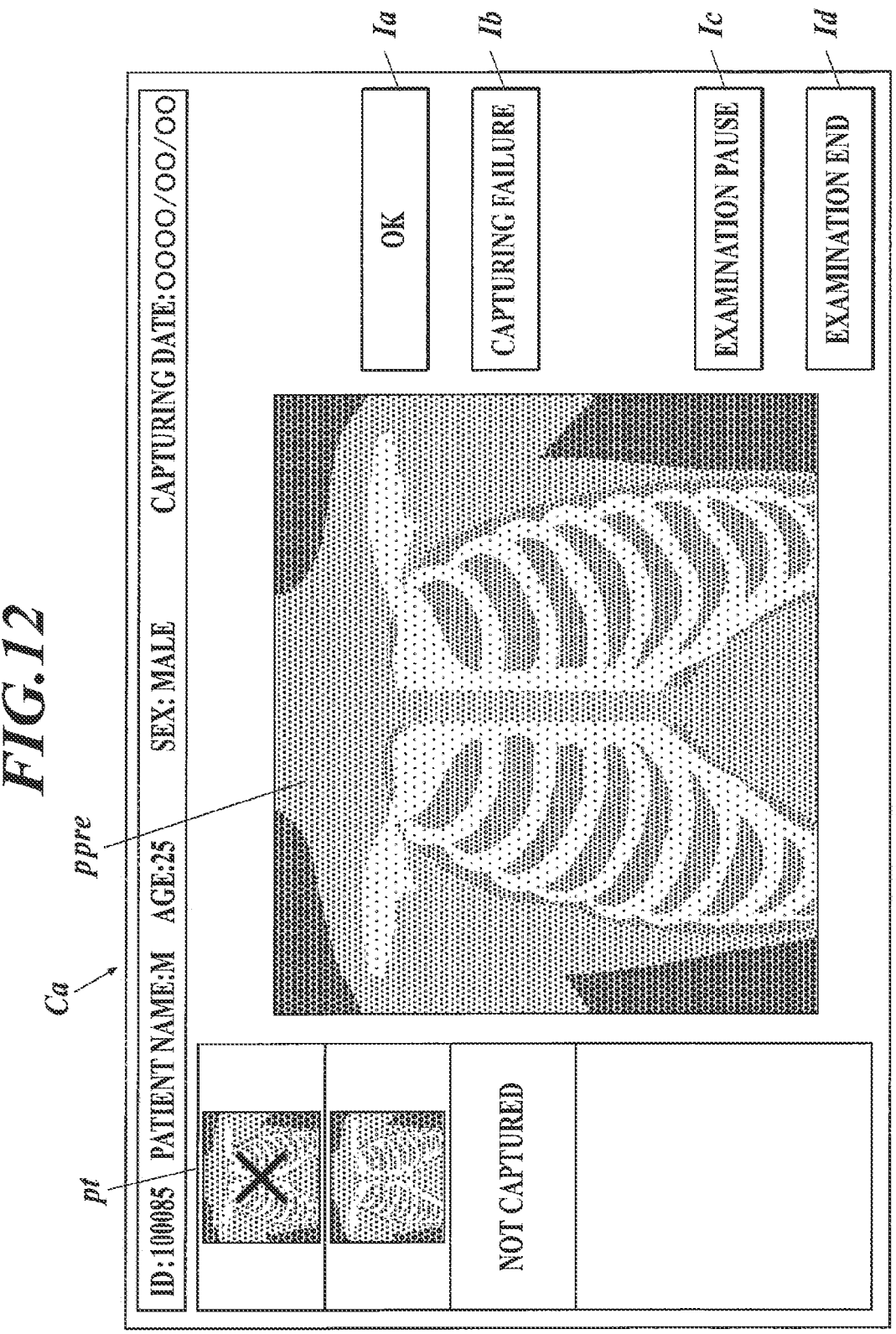
FIG. 12 is a diagram showing a state in which capturing is performed again and a preview radiation image is displayed on a display screen.

When the capturing is performed again and the preview signal value Dpre is transferred from the radiation image capturing apparatus 1, the console C generates the preview radiation image ppre based on the preview signal value Dpre, and displays the preview radiation image ppre on the display screen as shown in FIG. 12. According to the present embodiment, the thumbnail image pt (that is, the thumbnail image pt with the x mark) of the preview radiation image ppre considered to be the capturing failure is not deleted from the display screen and remains displayed on the left side of the display screen. The thumbnail image pt of the preview radiation image ppre captured again is displayed below the above.

According to the above configuration, when the series of capturing is performed, it is possible to accurately prevent the operator such as the radiation technician, etc. forgetting that the capturing failure occurred or in which radiation image p the capturing failure occurred (that is, which radiation image p is taken again).

When the operator such as the radiation technician, etc. approves the preview radiation image ppre (see FIG. 12) captured again, although illustration is omitted, similar to when the normal capturing is performed (see FIG. 9A), the parameters are written and stored in the storage destinations of the normal image irradiating amount information storage table T1 of the storage Cm. However, in this case, in the "CODE_MEANING", instead of "normal", the status of "re-capture" showing that the image is captured again is written.

Figure 13:
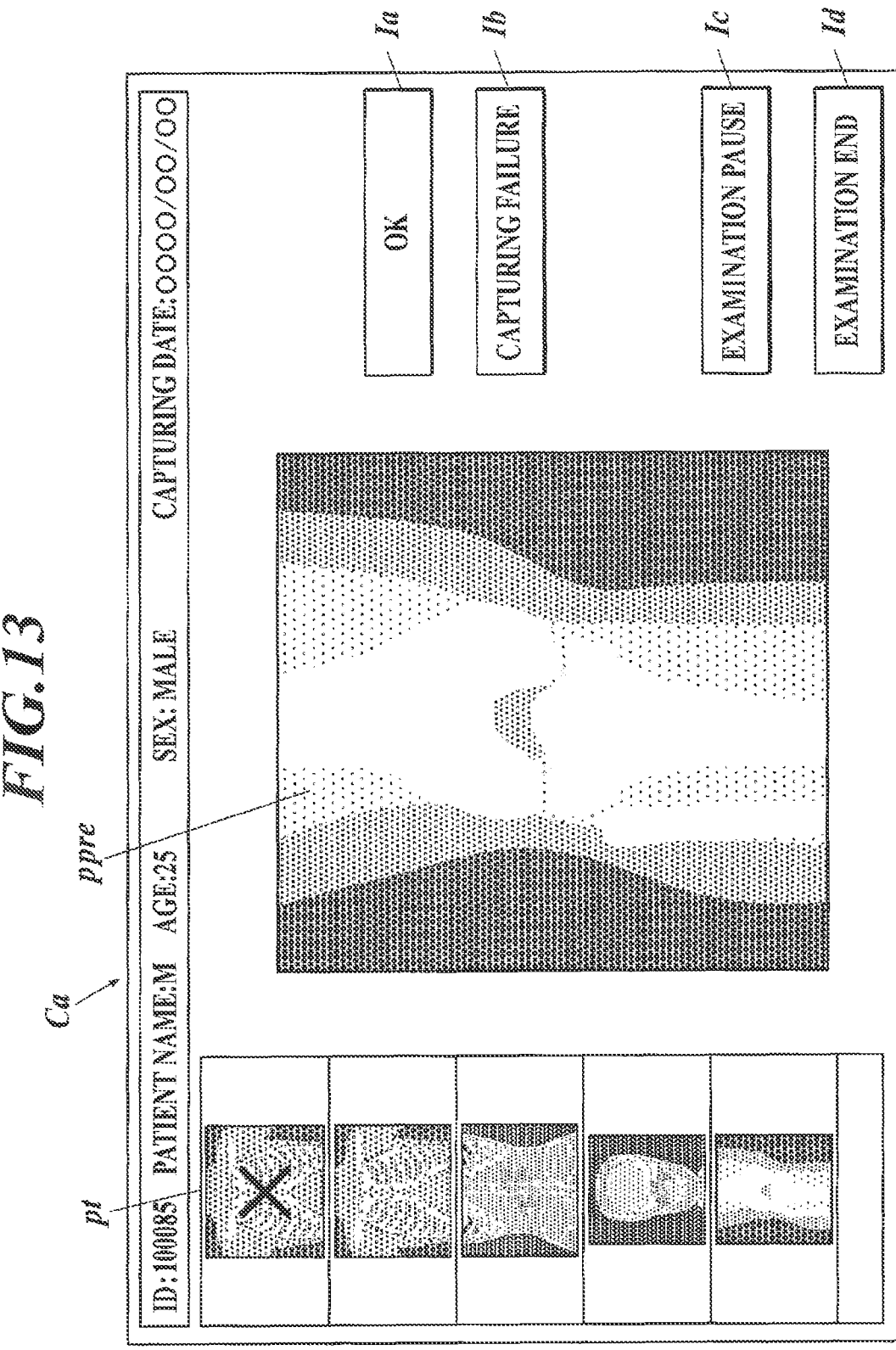
FIG. 13 is a diagram showing a state in which thumbnail images including a capturing failure are displayed aligned on a display screen when a string of capturing ends.

Then, for example, when the series of capturing is performed normally, the preview radiation image ppre is displayed in the center of the display screen for each capturing. Moreover, as shown in FIG. 13, the thumbnail image pt including the capturing failure is displayed aligned on the left side of the display screen. When such capturing is performed normally, as described above, the console C writes and stores the irradiating amount information such as the tube voltage and the capturing order ID, etc. of the capturing order information in the normal image irradiating amount information storage table T1 of the storage Cm.

As described above, capturing may be performed in addition to the series of capturing based on the capturing order information which the console C obtained from the RIS 101 in advance before capturing. The capturing order information regarding the additional capturing may be made on the spot or may be made later.

In this case, when the preview radiation image ppre additionally captured is approved by the operator such as the radiation technician, etc., although illustration is omitted, similar to when normal capturing is performed (see FIG. 9A), the parameters are written and stored in the storage destinations of the normal image irradiating amount information storage table T1 of the storage Cm. However, in this case, in the "CODE_MEANING", the status of "additional capturing" is written.

Then, when the series of capturing (series of capturing including the additional capturing when the additional capturing is performed) ends, and the operator such as the radiation technician, etc. clicks the "examination end" button icon Id on the display screen, the console C reads out from the storage Cm the irradiating amount information, etc. (see FIG. 9A and FIG. 11) written in the normal image irradiating amount information storage table T1 and the capturing failure image irradiating amount information storage table T2 for each capturing. As shown in FIG. 9B, the values (Value), that is, the parameter in the normal image irradiating amount information storage table T1 are tied to each tag (Tag) and are output to the RIS 101 with the information such as the capturing end time, etc. (MPPS (Completed)).

As for the irradiating amount information regarding the capturing of the radiation image p which is the capturing failure (that is, the irradiating amount information read out from the capturing failure image irradiating amount information storage table T2), the "code Meaning" shown in FIG. 9B is set as "capturing failure". As described in the above example, there are 4 capturing order information regarding the series of capturing which the console C obtains from the RIS 101 before capturing (see the 4 capturing order information regarding the patient "M" in FIG. 6), and when there is 1 capturing failure and the capture is performed again once, the irradiating amount information output from the console C to the RIS 101 is the irradiating amount information of capturing for a total of 5 times, 4 normal capturing, and 1 capturing failure.

When the operator such as the radiation technician, etc. clicks the "examination pause" button icon Ic (see FIG. 7, etc.) on the display screen in the middle of the series of capturing, as described above, the number of irradiating amount information output to the RIS 101 is the total of the number of the normal capturing and the number of the capturing failure which occurred until the capturing (examination) is paused (MPPS (Discontinued)).

Effect

As described above, according to the radiation image capturing system 100 of the present embodiment, not only the irradiating amount information regarding the normal capturing in the series of capturing but also the irradiating amount information regarding the capturing which is the capturing failure is also output to the RIS 101 which is the management system. Therefore, not only the irradiating amount information regarding the normal capturing but also the irradiating amount information regarding the capturing which is the capturing failure can be accurately and quantitatively managed with the management system such as the RIS 101, etc.

Therefore, for example, the next time that the operator such as the radiation technician, etc. performs capturing on the same patient (subject) using the same capturing apparatus in which capturing failure occurred in the past, it is possible to quantitatively understand how much the irradiating amount should be increased or decreased. Since it is possible to suitably and quantitatively increase or decrease the irradiating amount compared to the irradiating amount of the capturing when capturing failure occurred before, it is possible to reliably reduce the possibility of capturing failure occurring in future capturing. Therefore, it is possible to reliably reduce the possibility of increasing the amount of irradiation on the patient who is the subject due to capturing failure occurring and capturing being performed again.

The useful effect of the radiation image capturing system 100 regarding the present embodiment is not limited to the above. That is, according to the radiation image capturing system 100 of the present embodiment, as described above, the irradiating amount information of the irradiated radiation can be accurately managed for all capturing performed in the radiation image capturing system 100 including the capturing failure with the management system such as the RIS 101, etc.

For example, from the viewpoint of each patient, the radiation is irradiated on the patient not only when normal capturing is performed but also when capturing failure occurs. Since the irradiating amount information of the irradiated radiation for all capturing including the capturing failure is accurately managed in the radiation image capturing system 100 of the present embodiment, the total irradiating amount in the series of capturing including the capturing failure can be accurately and quantitatively acknowledged and managed for each patient.

Moreover, for example, by adding up the irradiating amount that a certain patient is irradiated in a certain term such as 1 month, 1 year or the like, it is possible to accurately and quantitatively acknowledge and manage the irradiating amount throughout a certain term for each patient.

According to the radiation image capturing system 100 of the present embodiment, as described above, the irradiating amount information of the irradiated radiation for all of the capturing including the capturing failure performed using the radiation image capturing system 100 can be centrally managed in the management system such as the RIS 101, etc.

Therefore, in the facilities such as the hospital, etc. including the radiation image capturing system 100, for example, it is possible to quantitatively manage how much radiation is irradiated in all capturing including the capturing failure in the entire facility within a predetermined term such as 1 day, 1 month, and the like. Therefore, it is possible to centrally and quantitatively manage the irradiating amount of the radiation in the facility.

By adding up the irradiating amount of the radiation irradiated for each modality, it is possible to quantitatively manage how much radiation is irradiated in all capturing including the capturing failure for each modality. With this, it is possible to centrally and quantitatively manage the irradiating amount of radiation for each modality.

[Processing when Capturing Failure is Cancelled]

When the preview radiation image ppre displayed on the display screen of the display Ca of the console C is considered to be the capturing failure (see FIG. 10), the capturing is performed again (see FIG. 12). However, the result of the capturing may be worse and the operator such as the radiation technician may cancel the capturing failure of the first captured image and may employ the first image.

Figure 14:
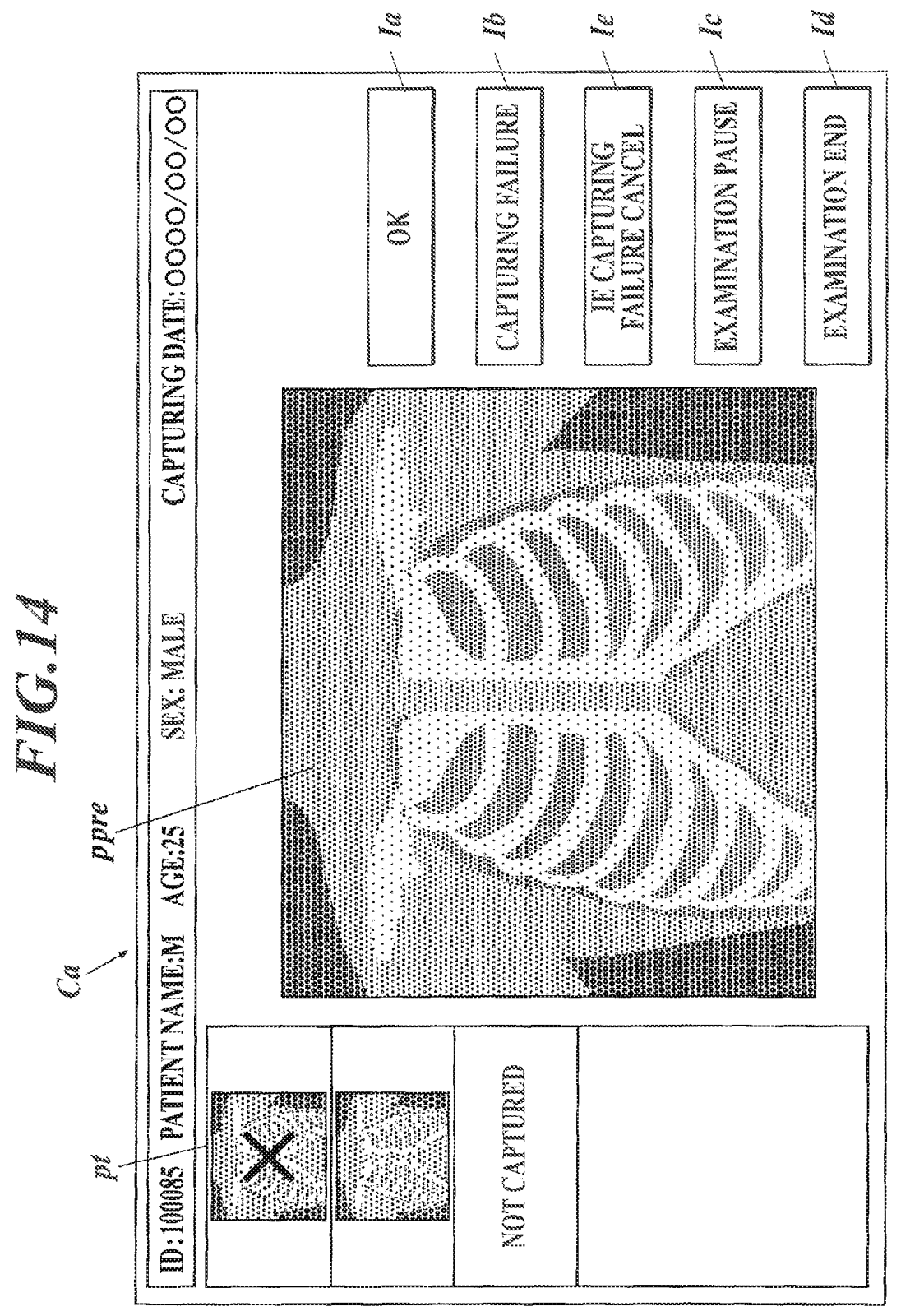

Therefore, in order to cope with the above situation, for example, as shown in FIG. 14, a "capturing failure cancel" button icon Ie can be provided on the display screen and the operator such as the radiation technician, etc. can click the "capturing failure cancel" button icon Ie so that the console C can perform the capturing failure cancel processing. When the capturing failure is canceled, instead of operating an icon, other operation can be performed to cancel the capturing failure.

In this case, when the operator such as the radiation technician, etc. clicks the "capturing failure cancel" button icon Ie and instructs cancelling of the capturing failure, the console C cancels the capturing failure of the previously captured image.

Figure 15:
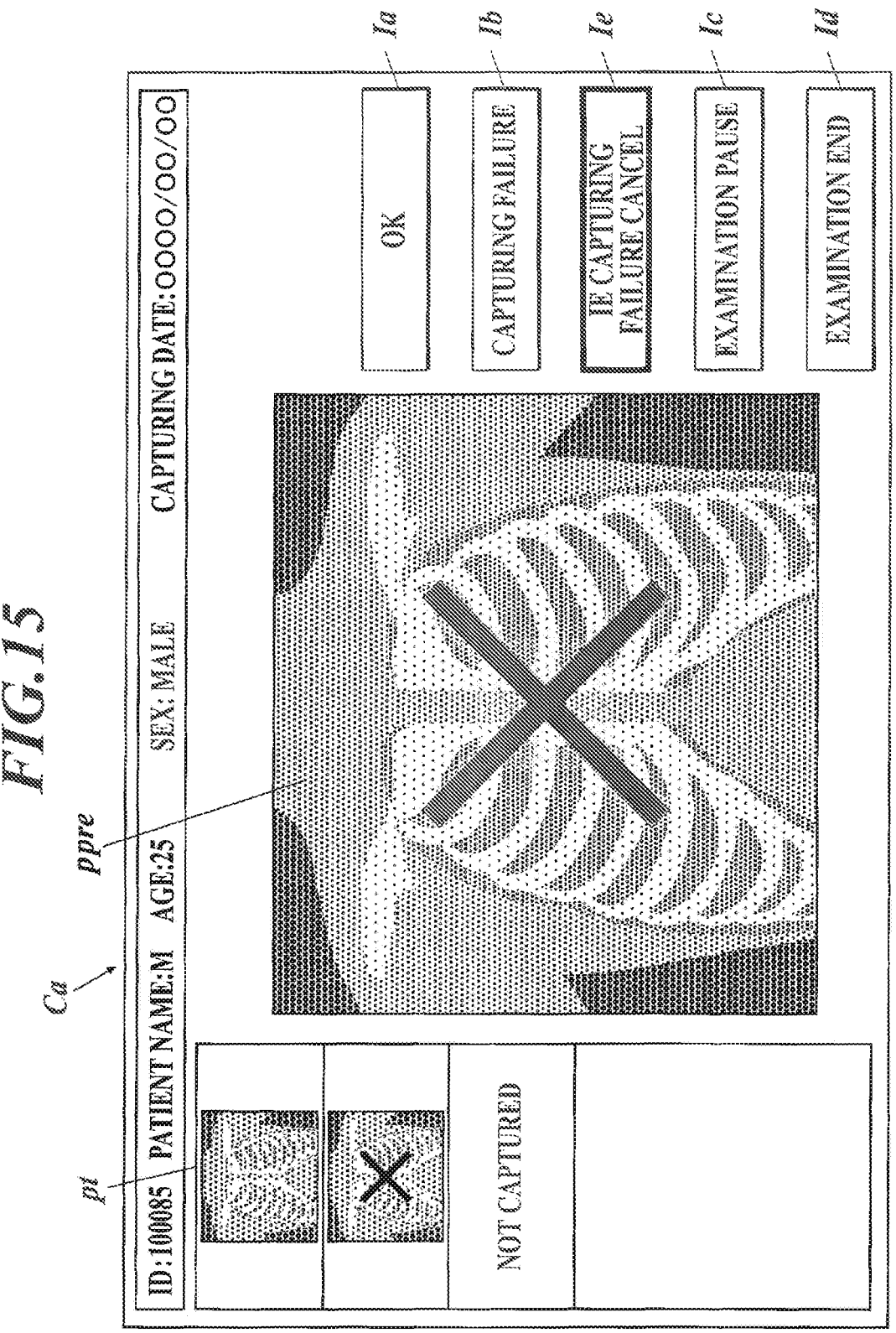
FIG. 15 is a diagram describing a display on the display screen changes when capturing failure cancel processing is performed.

Then, in this case, the console C may change the display from the thumbnail image pt (thumbnail image pt in the upper side of the drawing) of the image previously considered to be the capturing failure displayed with the x mark as shown in FIG. 14 to a display without the x mark as shown in FIG. 15.

In this case, the management of the irradiating amount information, etc. stored in the storage Cm needs to be switched. That is, when the Code Meaning (see FIG. 9B) in the irradiating amount information regarding the capturing previously considered to be the capturing failure is maintained "capturing failure" even when the judgment as the capturing failure is canceled, when the irradiating amount information, etc. is output to the RIS 101 as described above, the capturing is considered to be the capturing failure. In view of the above, the console C can perform the following processing.

For example, the console C reads out the irradiating amount information, etc. written and stored in the capturing failure image irradiating amount information storage table T2 (see FIG. 8 and FIG. 11) of the storage Cm regarding the capturing previously considered to be the capturing failure, and then moves and stores the above in the normal image irradiating amount information storage table T1 (see FIG. 8 and FIG. 9A) of the storage Cm. Here, the Code Meaning of the irradiating amount information, etc. becomes "normal" (or is rewritten).

Further, when the capturing previously considered to be the capturing failure is canceled and the Code Meaning of the irradiating amount information, etc. is "normal", the capturing performed again is not considered to be the capturing failure. For example, both the image which is previously considered to be the capturing failure but in which the capturing failure is canceled and the image which is captured again may be transferred to the external system such as PACS and confirmed by a physician who reads images or who performs diagnosis.

Therefore, in such case, the Code Meaning in the irradiating amount information is determined to be "normal" in both the capturing which is previously considered to be the capturing failure but in which the capturing failure is canceled and the capturing performed again. In this case, the Code Meaning in the irradiating amount information of the capturing which is employed by the physician who reads images or who performs diagnosis may be maintained as "normal" and the Code Meaning in the irradiating amount information of the capturing which is not employed may be rewritten as "capturing failure".

Moreover, for example, when the operator such as the radiation technician, etc. who determined that the result of the capturing performed again is worse clicks the "capturing failure" button icon Ib on the display screen with the preview radiation image ppre, etc. of the capturing performed again displayed and performs the capturing failure processing, the console C writes and stores the irradiating amount information, etc. of the capturing performed again in the capturing failure image irradiating amount information storage table T2 of the storage Cm and sets the Code Meaning of the irradiating amount information, etc. of the capturing performed again as "capturing failure". The console C may perform the capturing failure cancel processing by switching the irradiating amount information, etc. from the capturing failure image irradiating amount information storage table T2 to the normal image irradiating amount information storage table T1.

Instead of switching the irradiating amount information, etc. between tables, for example, the capturing failure cancel flag F can be used to perform the capturing failure cancel processing. That is, in this case, as shown in FIG. 16A, the capturing cancel flag F may be set in the irradiating amount information stored in the capturing failure image irradiating amount information storage table T2 of the storage Cm.

When the capturing failure occurs and the irradiating amount information, etc. is written and stored in the capturing failure image irradiating amount information storage table T2, as shown in FIG. 16A, the console C does not set the capturing failure cancel flag F (sets "0" in the capturing failure cancel flag F in FIG. 16A), the Code Meaning is set to "capturing failure", and the irradiating amount information, etc. is stored (processing as capturing failure).

Then, as described above, when the operator such as the radiation technician, etc. clicks the "capturing failure cancel" button icon Ie to instruct cancelling of the capturing failure after the capturing is performed again, as shown in "capturing 1" in FIG. 16B, the console C sets a capturing cancel flag F in the irradiating amount information regarding the previous capturing considered to be the capturing failure (in FIG. 16B, sets the capturing failure cancel flag F to "1") and cancels the capturing failure (capturing failure cancel processing).

In this case, when the Code Meaning of the irradiating amount information, etc. is set to "normal" as shown in FIG. 16B, when the irradiating amount information, etc. is output to the RIS 101, it is possible to more reliably prevent being considered to be a capturing failure.

As shown in "capturing 2" of FIG. 16B, the console C performs capturing failure processing on the capturing performed again and does not set the capturing failure cancel flag F for the capturing performed again (that is, the capturing failure cancel flag F is "0") and sets the Code Meaning as "capturing failure" in the irradiating amount information for the capturing performed again, and writes and stores the above in the capturing failure image irradiating amount information storage table T2 (processing as capturing failure).

Then, according to such configuration, the console C is able to perform capturing failure cancel processing with the irradiating amount information, etc. stored in the capturing failure image irradiating amount information storage table T2. With this, the console C is able to output the irradiating amount information, etc. regarding the previous capturing in which the judgment of capturing failure is canceled to the RIS 101 as the irradiating amount information, etc. regarding normal capturing instead of capturing failure.

The present invention is not limited to the above embodiment, and the present invention can be suitably changed without leaving the scope of the present invention.

The present U.S. patent application claims priority under the Paris Convention of Japanese Patent Application No. 2016-028512 filed on Feb. 18, 2016 the entirety of which is incorporated herein by reference.

What is claimed is:

1. A radiation image capturing system comprising:
    an input unit to receive an input from a user that designates a first captured radiation image as a capturing failure;
    a storage which stores irradiating amount information regarding capturing set as the capturing failure when there is input that the first captured radiation image is the capturing failure, wherein the stored irradiating amount information indicates an irradiating amount of the capturing when the capturing failure occurred;
    an output unit which outputs the irradiating amount information regarding the capturing set as the capturing failure stored in the storage,
    wherein the input unit is configured to receive a further input to cancel the capturing failure designation of the first captured radiation image, and
    when the first captured radiation image is designated as the capturing failure and is captured again as a second captured radiation image, both the irradiating amount information for the first captured radiation image and the irradiating amount information for the second captured radiation image are stored corresponded to one capturing order information.

2. The radiation image capturing system according to claim 1, wherein, the output unit outputs the irradiating amount information regarding the capturing set as the capturing failure stored in the storage.

3. The radiation image capturing system according to claim 2, further comprising a console which generates the radiation image based on a signal value transferred from a radiation image capturing apparatus which reads out radiation passing through a subject as the signal value,
    wherein, the output unit is controlled by the console; and the storage is storage performed in the console.

4. The radiation image capturing system according to claim 3, further comprising an order obtaining unit which obtains capturing order information from a management system,
    wherein, the order obtaining unit obtains the capturing order information in the console.

5. The radiation image capturing system according to claim 1, wherein, the irradiating amount information regarding the capturing of a radiation image set as the capturing failure includes at least one among a tube voltage, a tube current, an exposure time, and an irradiating amount set in a radiation generating apparatus when the capturing is performed.

6. The radiation image capturing system according to claim 1, wherein, the irradiating amount information regarding the capturing of a radiation image set as the capturing failure includes irradiating amount of radiation irradiated to a radiation image capturing apparatus which captures the radiation image when the capturing is performed.

7. The radiation image capturing system according to claim 1, wherein, the irradiating amount information regarding the capturing of a radiation image set as the capturing failure includes irradiating amount of radiation irradiated from a radiation generating apparatus when the capturing is performed.

8. The radiation image capturing system according to claim 1,
    wherein, the output unit outputs to a management system that irradiating amount information for which the capturing failure cancel is instructed by the input unit is irradiating amount information which is not the capturing failure.

9. The radiation image capturing system according to claim 1, further comprising a management system that manages the irradiating amount information of the irradiated radiation for the capturing including the capturing failure.

10. The radiation image capturing system according to claim 1, wherein the irradiating amount information indicates an increase or decrease of the irradiating amount of capturing when the capturing failure occurred that is required to achieve a normal capturing.

11. The radiation image capturing system according to claim 1, wherein the captured radiation image is displayed on a display, and
    the input unit inputs that the first captured radiation image displayed on the display is the capturing failure.

12. The radiation image capturing system according to claim 11, wherein the input unit inputs that the first captured radiation image is the capturing failure on a display screen where the captured radiation image is displayed, the display screen being displayed on the display.

13. The radiation image capturing system according to claim 1, wherein a normal image irradiating amount information indicates an irradiating amount of the capturing when the capturing is not a capturing failure, the normal image irradiating amount information and the capturing failure image irradiating amount information are stored in separate irradiating amount in formation storage tables.

14. The radiation image capturing system according to claim 1, wherein the irradiating amount information is stored in an irradiating amount information storage table and the capturing failure is indicated by a flag in the irradiating amount information storage table.

* * * * *